US 6,500,810 B2

(12) United States Patent
Lefer et al.

(10) Patent No.: US 6,500,810 B2
(45) Date of Patent: Dec. 31, 2002

(54) METHOD OF REGULATING EXPRESSION OF ADHESION MOLECULES ON CIRCULATING LEUKOCYTES

(75) Inventors: Allan M. Lefer, Huntingdon Valley, PA (US); J. Graham Goddard, San Francisco, CA (US)

(73) Assignee: Sky High, LLC, Evanston, IL (US)

( * ) Notice: Subject to any disclaimer, the term of this patent is extended or adjusted under 35 U.S.C. 154(b) by 0 days.

(21) Appl. No.: 09/738,411

(22) Filed: Dec. 14, 2000

(65) Prior Publication Data

US 2001/0049362 A1 Dec. 6, 2001

Related U.S. Application Data

(60) Provisional application No. 60/170,929, filed on Dec. 14, 1999.

(51) Int. Cl.[7] ..................... A61K 31/685; A61K 31/61; A61K 31/70
(52) U.S. Cl. ............................ 514/78; 514/77; 514/75; 514/25
(58) Field of Search ..................... 514/78, 75, 25, 514/77; 424/450

(56) References Cited

U.S. PATENT DOCUMENTS

| | | | | |
|---|---|---|---|---|
| 4,647,586 A | * | 3/1987 | Mizushima et al. | 514/532 |
| 5,567,425 A | * | 10/1996 | Bathurst et al. | 424/195.1 |
| 5,889,011 A | | 3/1999 | Klein et al. | 514/263 |
| 5,961,970 A | * | 10/1999 | Lowell et al. | 424/93.1 |
| 6,004,579 A | * | 12/1999 | Bathurst et al. | 424/450 |
| 6,008,205 A | * | 12/1999 | Serhan et al. | 514/102 |
| 6,100,271 A | | 8/2000 | Klein et al. | 514/263 |

FOREIGN PATENT DOCUMENTS

JP     58-150508     *  7/1983

OTHER PUBLICATIONS

"Lysophosphatidylcholine stimulates leukocyte rolling and adherence in rat mesenteric microvasculature", Lefer et al., American Journal of Physiology, 1997, vol. 272., No. 6 Part 2, pp. H2584–H2590, abstract.*
"Drug R & D News Digest: Drugs in Preclinical Study", Media Release, 1998.*
Database Biosis on STN, Biological Abstracts, No. BA94:128522, Kume et al., Abstract, *J. Clin. Invest.* 1992, 90(3): 1138–1144.

* cited by examiner

*Primary Examiner*—Zohreh Fay
*Assistant Examiner*—Brian-Yong S. Kwon
(74) *Attorney, Agent, or Firm*—Sheridan Ross P.C.

(57) ABSTRACT

A method to inhibit inflammation in a mammal is disclosed. The method includes administering to the mammal a composition comprising a phospholipid, which can be lysophosphatidic acid. The administration of a phospholipid is believed to down regulate expression of adhesion molecules on the surface of vascular endothelial cells and circulating leukocytes of the mammal.

8 Claims, 13 Drawing Sheets

METHOD OF REGULATING EXPRESSION OF ADHESION MOLECULES ON CIRCULATING LEUKOCYTES

CROSS REFERENCE TO RELATED APPLICATION

This application claims priority under 35 U.S.C. §119(e) from U.S. Provisional Application No. 60/170,929, filed Dec. 14, 1999, which is incorporated herein by reference in its entirety.

REFERENCE TO GOVERNMENT SUPPORT

The present invention was supported in part by Research Grant No. GM45434 from the National Institute of General Medical Sciences of the NIH. Therefore, the United States government may have certain rights in the invention.

BACKGROUND OF THE INVENTION

The present invention relates to the use of phospholipid compositions to attenuate inflammation.

The inflammatory response is characterized by increased leukocyte rolling, adherence and transmigration following an inflammatory stimulus. The early hallmark of endothelial dysfunction is reduced release of nitric oxide (NO), which not only regulates vascular tone, but also modulates leukocyte-endothelium interaction. Leukocyte-endothelium interaction represents a multistep process involving sequential activation of specific cell adhesion glycoproteins such as integrins, immunoglobulin superfamily members and selectins (Bevilacqua & Nelson, 1993; McEver, 1992). Two of these adhesion molecules are particularly important in the regulation of cell-to-cell interaction (i.e., P-selectin on the microvascular endothelium and CD18 on circulating neutrophils).

In particular, P-selectin, a member of the selectin family of adhesion glycoproteins, is rapidly translocated from the Weibel-Palade bodies to the endothelial cell surface upon hypoxia-reoxygenation or activation with inflammatory mediators such as thrombin, histamine, or oxygen-derived free radicals (Lorant et al., 1991; McEver et al., 1989; Patel et al., 1991). P-selectin is believed to play a significant role in the initial phase of leukocyte capture, which is rolling of leukocytes along the vascular endothelial surface (McEver et al., 1989; Davenpeck et al., 1994). PMN rolling serves to tether the unstimulated neutrophil to the activated endothelium, thus bringing the neutrophil in closer contact with the endothelial cells, allowing firm adherence to occur (Lorant et al., 1991; Davenpeck et al., 1994). Rolling PMNs are able to engage in firm adhesion to the endothelium mainly by $\beta_2$-integrin interacting (i.e., CD11/CD18) with intercellular adhesion molecule-1 (CAM-1)(Butcher, 1991). Following adhesion, PMNs are further activated, change their shape, and some undergo transendothelial migration mediated in large part by PECAM-1 (Vaporciyan et al., 1993). Finally, activated leukocytes can release superoxide radicals, which can directly quench endogenous NO released by endothelial cells (Rubanyi & Vanhoutte, 1986; Ma et al., 1993), a process known to exacerbate endothelial dysfunction.

A functional relationship between the loss of endothelium-derived NO and the expression of P-selectin has been established (Davenpeck et al., 1994). Similarly, it has been shown that blocking NO synthesis via $N^G$-monomethy-[-L-arginine or $N^G$-nitro-LCarginine methyl ester (L-NAME) increases leukocyte adherence and emigration in the mesenteric microcirculation (Scalia & Leer, 1998) as well as enhances microvascular permeability (Kubes & Granger, 1992).

Thus, a need exists for methods of attenuating the inflammation process by modulating the expression of adhesion molecules in endothelial cells or circulating neutrophils. The present invention satisfies this needs and provides related advantages as well.

DETAILED DESCRIPTION OF THE INVENTION

Figure 1:
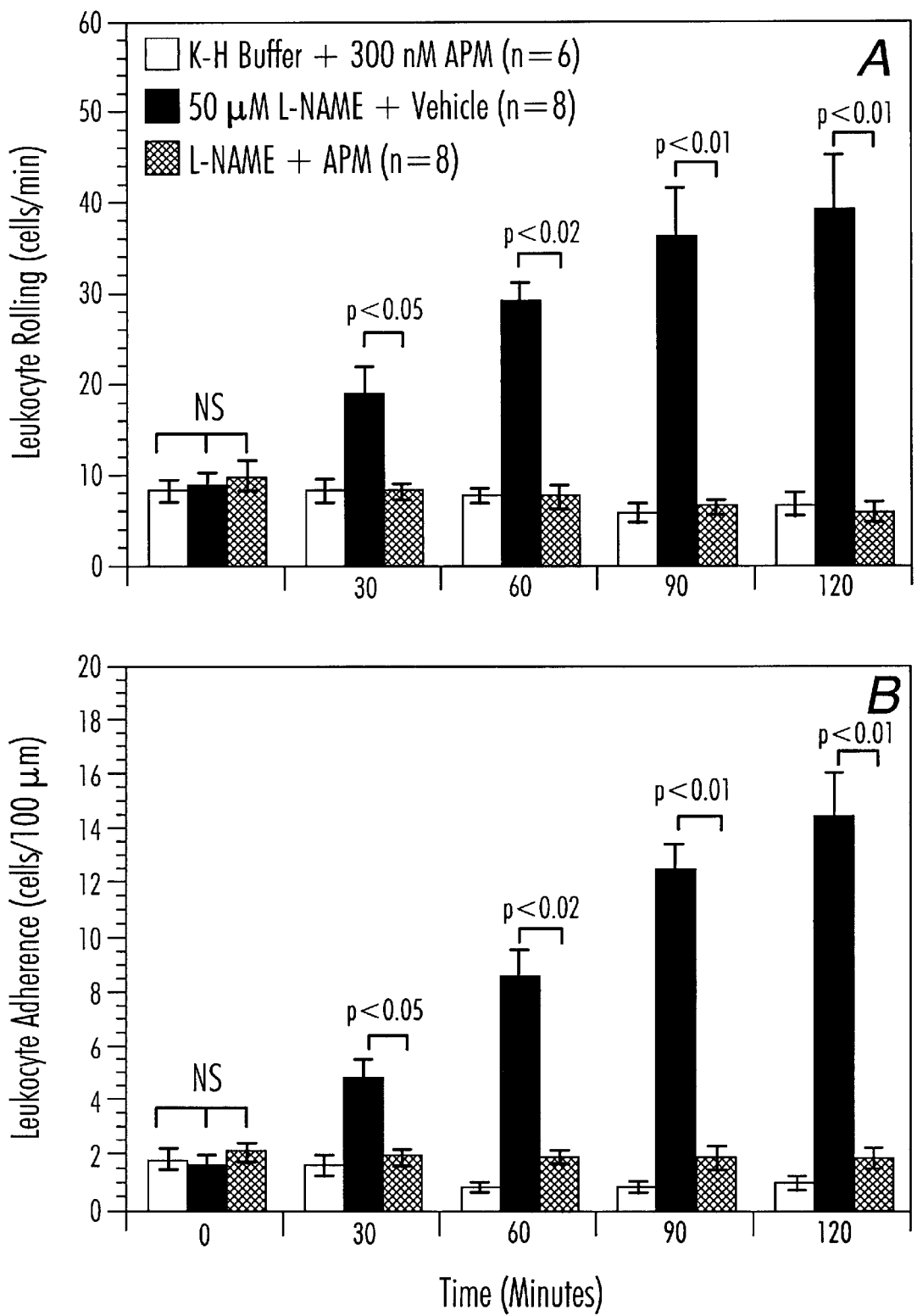
FIG. 1 shows the time course of leukocyte rolling (panel A) and leukocyte adherence (panel B) in rat mesenteric venules. Superfusion of the mesentery with 50 μM L-NAME significantly increased leukocyte rolling and leukocyte adherence in the rat mesenteric microvasculature. Concomitant superfusion of the rat mesentery with APM attenuated L-NAME-induced leukocyte rolling and adherence. Bar heights represent mean values; brackets indicate ±SEM. Numbers in parentheses indicate numbers of rats studied.

The present invention relates to methods of administering an effective amount of a phospholipid or a mixture of phospholipids to inhibit inflammation. Such methods are generally accomplished by administering to a patient an effective amount of a lysophosphatidic acid (LPA), a LPA analog, or a composition containing LPA to prevent, reduce or otherwise inhibit inflammation. The method of the present invention can be used in any animal as a patient, and particularly, in any mammal, including, without limitation, primates, rodents, livestock and domestic pets. Preferred mammals to treat using the method of the present invention include humans.

The LPA-containing compositions useful in the methods of the present invention include those described in WO 99/47101 and WO 97/09989, both incorporated herein by reference. Suitable LPA-containing formulations include, for example, a sonicated mixture of soy-derived phospholipids, referred to herein as "APM," which contains phosphatidic acid (PA), phosphatidyl inositol (PI), lysophosphatidic acid (LPA), lysophosphatidyl choline (LPC) and lysophosphatidyl inositol (LPI) in a ratio by weight of 10:10:8:4:2, respectively. APM is described in WO 97/09989. Another useful formulation containing these phospholipids is known as LXR-015, which is described in Umansky et al., 1997 and Wu et al., 1997, both incorporated herein by reference. This class of LPA-containing formulations has been shown to prevent apoptotic cell death both in vitro and in vivo (Umansky et al., 1997). In vitro data obtained with LXR-015 have clearly demonstrated inhibition of apoptotic cell death in rat neonatal cardiac myocytes exposed to either serum-glucose deprivation or simulated ischemia-reperfusion (Umansky et al., 1997). A similar action is demonstrable also in vivo in which LXR-015 has been shown to improve hypothermic preservation of the rat liver (Wu et al., 1997). However, none of these publications addressed the role of these LPA-containing formulations in inhibiting inflammation.

In the present invention, such LPA, LPA analogs and mixtures containing LPA can be used as the sole active ingredient. Optionally, other useful therapeutic agents, including without limitation biodegradable polymers, pharmaceutically acceptable excipients and pharmaceutically effective agents, such as drugs, antibiotics, wound healing agents, antioxidants, and other anti-inflammatory agents, such as those described, for example, in WO 99/47101, incorporated herein by reference, can be included in the compositions to be administered.

Methods of making and administering the LPA-containing compositions are described in WO 99/47101 and WO 97/09989, both incorporated herein by reference. Those skilled in the art can readily determine based on the teachings herein and in WO 99/47101 and WO 97/09989, both incorporated herein by reference, the effective amounts of such compositions useful in inhibiting inflammation.

The compositions are particularly useful in blocking or inhibiting several inflammatory responses. Such inflammatory responses include endothelial, leukocyte and/or neutrophil cell activation in response to an inflammatory stimuli. In addition, the compositions can block or inhibit the expression or appearance of adhesion molecules on the cell surfaces of endothelial and/or leukocyte cells.

REFERENCES CITED

Bevilacqua, M. P. and Nelson, R. M. (1993) Endothelial-leukocyte adhesion molecules in inflammation and metastasis. *Thromb. Haemost.* 70, 152–154.

Borders, J. L. and Granger, H. J. (1984) An optical doppler intravital velocimeter. *Microvasc. Res.* 27, 117–127.

Butcher, E. C. (1991) Leukocyte-endothelial cell recognition: three (or more) steps to specificity and diversity. *Cell* 67, 1033–1036.

Davenpeck, K. L., Gauthier, T. W., Albertine, K. H., and Lefer, A. M. (1994) Role of P-selectin in microvascular leukocyte-endothelial interaction in splanchnic ischemia-reperfusion. *Am. J. Physiol.* 267, H622–H630.

Davenpeck, K. L., Gauthier, T. W., and Lefer, A. M. (1994) Inhibition of endothelial-derived nitric oxide promotes P-selectin expression and actions in the rat microcirculation. *Gastroent.* 107, 1050–1058.

Entman, M. L., Michael, L., Rossen, R. D., Dreyer, W. J., Anderson, D. C., Taylor, A. A., and Smith, C. W. (1991) Inflammation in the course of early myocardial ischemia. *FASEB J.* 5, 2529–2537.

Granger, D. N., Benoit, J. N., Suzuki, M., and Grisham, M. B. (1989) Leukocyte adherence to venular endothelium during ischemia-reperfusion. *Am. J. Physiol.* 257, G683–G689.

Kubes, P. and Granger, D. N. (1992) Nitric oxide modulates microvascular permeability. *Am. J. Physiol.* 262, H611–H618.

Kubes, P., Suzuki, M. and Granger, D. N. (1991) Nitric oxide: an endogenous modulator of leukocyte adhesion. *Proc. Natl. Acad. Sci. USA,* 88, 4651–4655.

Lefer, A. M. and Lefer, D. J. (1996) The role of nitric oxide and cell adhesion molecules on the microcirculation in ischemia-reperfusion. *Cardiov. Res.* 32, 743–751.

Lorant, D. E., Patel, K. D., McIntyre, T. M., McEver, R. P., Prescott, S. M., and Zimmerman, G. A. (1991) Coexpression of GMP-140 and PAF by endothelium stimulated by histamine or thrombin: a juxtacrine system for adhesion and activation of neutrophils. *J. Cell Biol.,* 115, 223–234.

Lorant, D. E., Topham, M. K., Whatley, R. E., McEver, R. P., McIntyre, T. M., Prescott, S. M., and Zimmerman, G. A. (1993) Inflammatory roles of P-selectin. *J. Clin. Invest.,* 92, 559–570.

Ma, X. L., Weyrich, A. S., Lefer, D. J., and Lefer, A. M. (1993) Diminished basal nitric oxide release after myocardial ischemia and reperfusion promotes neutrophil adherence to coronary endothelium. *Circ. Res.* 72, 403–412.

McEver, R. P., (1992) Leukocyte-endothelial cell interactions. *Curr. Opin. Cell Biol.* 4, 840–849.

McEver, R. P., Beckstead, J. H., Moore, K. L., Marshall-Carlson, L., and Bainton, D. F. (1989) GMP-140, a platelet alpha-granule membrane protein, is also synthesized by vascular endothelial cells and is localized in Weibel-Palade bodies. *J. Clin. Invest.* 84, 92–99.

Patel, K. D., Zimmerman, G. A., Prescott, S. M., McEver, R. P., and McIntyre, T. M. (1991) Oxygen radicals induce human endothelial cells to express GMP-140 and bind neutrophils. *J. Cell Biol.* 112, 749–759.

Rubanyi, G. M. and Vanhoutte, P. M. (1986) Oxygen-derived free radicals, endothelium, and responsiveness of vascular smooth muscle. *Am. J. Physiol.* 250, H815–H821.

Scalia, R., Armstead, V. E., Minchenko, A., and Lefer, A. M. (1999) Essential Role of P-Selectin in the Initiation of the Inflammatory Repose Induced by Hemorrhage and Reinfusion. *J. Exp. Med., In press.*

Scalia, R., Gefen, J., Petasis, N. A., Serhan, C. N., and Lefer, A. M. (1997) Lipoxin A4 stable analogs inhibit leukocyte rolling and adherence in the rat mesenteric microvasculature: role of P-selectin. *Proc. Natl. Acad. Sci USA* 94, 9967–9972.

Scalia, R. and Lefer, A. M. (1998) In vivo regulation of PECAM-1 activity during acute endothelial dysfunction in the rat mesenteric microvasculature. *J. Leukoc. Biol.* 64, 163–169.

Tsao, P. S. and Lefer, A. M. (1990) Time course and mechanism of endothelial dysfunction in isolated ischemic- and hypoxic-perfused rat hearts. *Am. J. Physiol.* 259, t-6.

Umansky, S. R., Shapiro, J. P., Cuenco, G. M., Foehr, M. W., Bathurst, I. C., and Tomei, L. D. Prevention of rat neonatal cardiomyocyte apoptosis induced by simulated in vitro ischemia and reperfusion. *Cell Death Differ* 4, 608–616, 1997.

Umansky, S. R. and Tomei, L. D. (1997) Apoptosis in the heart. *Adv. Pharmacol.* 41, 383–407.

Vaporciyan, A. A., DeLisser, H. M., Yan, H. C., Mendiguren, I. I., Thom, S. R., Jones, M. L., Ward, P. A. and Albelda, S. M. (1993) Involvement of platelet-endothelial cell adhesion molceule-1 in neutrophil recruitment in vivo. *Science* 262, 1580–1582.

Vedder, N. B., and Harlan, J. M. (1988) Increased surface expression of CD11b/CD18 (Mac-1) is not required for stimulated neutrophil adherence to cultured endothelium. *J. Clin. Invest.*, 81, 676–682.

Weyrich, A. S., Buerke, M., Albertine, K. H., and Lefer, A. M. (1995) Time course of coronary vascular endothelial adhesion molceule expression during reperfusion of the ischemic feline myocardium. *J. Leukoc. Biol.* 57, 45–55.

Williams, J. H. J., Moser, K. M., Ulich, T., and Cairo, M. S. (1987) Harvesting the noncirculating pool of polymorphonuclear leukocytes in rats by hetastarch exchange transfusion (HET): yield and functional assessment. *J. Leukoc. Biol.* 42, 455–462.

Wu, G., Tomei, L. D., Bathurst, I. C., Zhang, F. Hong, C. B., Issel, C. J., Columbano, A., Salley, R. K., and Chien, S. (1997) Antiapoptotic compound to enhance hypothermic liver preservation. *Transplantation* 63, 803–809.

The following experimental results are provided for the purposes of illustration and are not intended to limit the scope of the invention.

EXAMPLE 1

Animal Preparation

Male Sprague-Dawley rats, weighing 250–275 g, were anesthetized by intraperitoneal injection of sodium pentobarbital (60 mg/kg). A tracheotomy was performed to maintain a patent airway throughout the study. A polyethyene catheter (PE50) was inserted in the left carotid artery to monitor mean arterial blood pressure (MABP). The jugular vein was also cannulated for addition of supplementary anesthetic or for blood withdrawal-reinfusion. The abdominal cavity was opened via a midline laparotomy as previously described in Scalia et al., *Proc. Natl. Acad. Sci. U.S.A.*, 94:9967–9972 (1997). A loop of ileal mesentery was exteriorized through the midline incision and placed in a temperature controlled fluid-filled Plexiglas chamber and transilluminated for observation of the mesenteric microcirculation via intravital microscopy.

EXAMPLE 2

Intravital Microscopy of the Rat Mesentery

The ileum and mesentery were superfused throughout the experiment with a modified Krebs-Henseleit (K-H) according to a procedure reported in Scalia et al., *Proc. Nat'l Acad. Sci. U.S.A.*, 94:9967–9972(1997). A Microphot microscope and a 40× water immersion lens (Nikon Corp., Tokyo, Japan) were used to visualize the mesenteric microcirculation and the mesenteric tissue. The image was projected by a CCD video camera (DC-330, DAGE-MTI, Inc., Michigan City, Ind.) onto a color Sony high resolution video monitor (Multiscan 200-sf), and the image recorded with a videocassette recorder. All images were then analyzed using computerized imaging software (Phase 3 Image System, Media Cybernetics) on a Pentium based IBM-compatible computer (Micro Millenia Mxe, Micron Electronics Inc., Nampa, Id.). Red blood cell velocity was determined on-line using an optical doppler velocimeter (Borders & Granger, *Microvas. Res.* 27:117–127 (1984)) obtained from the Microcirculation Research Institute, College Station, Tex. This method gives an average red blood cell velocity, which is digitally displayed on a meter, and allows for the calculation of shear rates (Granger et al., *Am. J. Physiol.*, 257:G683–G689 (1989)).

After a 20–30 minutes stabilization period, a 30–50 mm diameter post-capillary venule was chosen for observation. The number of rolling, adhered and transmigrated leukocytes was determined off-line by playback analysis of the videotape. Leukocytes were considered to be rolling if they were moving at a velocity significantly slower than that of red blood cells. Leukocyte rolling is expressed as the number of cells moving past a designated point per minute (i.e., leukocyte flux). A leukocyte was judged to be adherent if it remained stationary for more than 30 seconds. Adherence is expressed as the number of leukocytes adhering to the endothelium/100 $\mu$m of vessel length. Transmigrated leukocytes were determined in an area covering a distance of 20 $\mu$m in either direction from the vessel wall. The number of extravasated leukocytes was counted an normalized with respect to area (20 $\mu$m×100 $\mu$m).

Activation of leukocyte-endothelium interactions in the rat mesenteric microcirculation was induced by either superfusion of the rat mesentery with the nitric oxide synthase inhibitor L-NAME, or by hemorrhage and reinfusion, according to the following experimental protocols.

A. L-NAME Superfusion Protocol

Rats were randomly divided into one of four groups: (1) K-H solution superfused rats (n=6); (2) K-H solution superfused rats also superfused with 300 nM APM (n=6); (3) 50 $\mu$M L-NAME superfused rats also superfused with vehicle (n=8); (4) 50 $\mu$M L-NAME superfused rats also superfused with 300 $\mu$M APM (n=8). A baseline recording was made to establish basal values for leukocyte rolling, adherence and transmigration (time 0). Immediately thereafter, L-NAME superfusion of the mesentery was started. Video recordings were made at 30, 60, 90 and 120 minutes after initiation of superfusion for quantification of leukocyte rolling, adherence and transmigration. In an additional group of L-NAME superfused rats (n=5), superfusion of APM was discontinued after 30 minutes and the effects of L-NAME alone on leukocyte-endothelium interaction were continuously monitored for an additional period of 90 minutes.

B. Hemorrhagic Shock Protocol

Rats were subjected to hemorrhage by withdrawal of blood to allow MABP to be maintained at 45 mmHg for 90 minutes. The mean bleedout volumes were 46±2 ml/kg and 46±1.8 ml/kg for the hemorrhage+vehicle and for hemorrhage+APM groups, respectively. Blood was collected in a heparinized (50 U) syringe, and kept at 37° C. until reinfusion. Rats were then resuscitated by infusion of the shed blood. Rats were sacrificed by overdose of pentobarbital 90 minutes after resuscitation, when intravital microscopy studies were completed. Control rats underwent cannulation and anesthesia for an identical period of time as hemorrhages rats, but were not bled. Rats were randomly assigned to one of three experimental groups: (1) sham operated rats superfused with 300 nM APM (n=6), (2) hemorrhage rats superfused with vehicle (n=6), and (3) hemorrhage rats superfused with 300 nM APM (n=7). Video recordings were made at 0, 30, 60, 90, 120 and 180 minutes for quantification of leukocyte rolling, adherence and transmigration.

The total number of circulating white blood cells in the three experimental groups of rats was determined by hemocytometric count of blood smears obtained from collection of blood through the jugular vein cannula.

EXAMPLE 3

Immunolocalization of P-Selectin in the Rat Mesenteric Vasculature

Immunohistochemical localization of P-selectin was determined in ileal samples after intravital microscopy was completed, according to methods described in Scalia et al., *Proc. Nat'l Acad. Sci. U.S.A.*, 94:9967–9972 (1997). Monoclonal antibody (mAb) PB1.3 only recognizes surface expressed P-selectin as described in Weyrich et al., *J. Leukoc. Biol.*, 57:45–55 (1995). Quantification of P-selectin was accomplished using the avidin-biotin immunoperoxidase technique (Vectastain ABC Reagent, Vector Laboratories, Burlingame, Calif.) as described by Weyrich et al., supra. Fifty venules were analyzed per tissue section, twenty sections were examined per group, and the percentage of positive staining venules was tallied.

EXAMPLE 4

Flow Cytometry of Isolated Rat Neutrophils

Flow cytometric analysis of CD18 complex in rat neutrophils was performed according to standard procedures as described in Vedder & Harlan, *J. Clin. Invest.*, 81:676–682 (1988). Rat neutrophils were freshly isolated from rat whole blood according to the method of Williams et al., *J. Leukocyte Biol.*, 42:455–462 (1987). Isolated neutrophils were washed twice in calcium-free Tyrode's solution containing 0.2% bovine serum albumin (BSA) and suspended in RPMI1630 medium. Neutrophils (5×105 cells/tube) were incubated with a monoclonal antibody directed against CD18 (Endogen, Boston, Mass.) at 4° C. for 30 minutes. Excess primary antibody was then removed by washing the platelets or neutrophils in RPMI1630. A goat anti-human gig F(AB')2 FITC conjugate was used as the secondary antibody at a 1:100 dilution (4° C. for 30 minutes). The stained neutrophils were washed twice with RPMI1630 and finally fixed in 1% paraformaldehyde, and then analyzed by flow cytometry (FACScan, Becton-Dickinson, San Jose, Calif.).

EXAMPLE 5

Statistical Analysis

All values for data listed herein and the figures are presented as means ± standard errors of the mean (SEM) of n independent experiments. Data were compared by analysis of variance (ANOVA) using post-hoc analysis with Fishers correct t-test. Probabilities of 0.05 or less were considered significant in all cases.

EXAMPLE 6

Results and Discussion

A. Effect of APM on L-NAME Induced Leukocyte-Endothelial Cell Interaction

There was no difference in the initial mean arterial blood pressure among the three groups of rats after all surgical procedures were performed. Mean arterial blood pressures ranged between 129±4 and 130±3 mmHg over the two hour observation period. Moreover, no significant systemic effect was observed after exposure of the rat mesentery to either L-NAME alone or L-NAME plus 300 nM APM, as confirmed by the absence of any significant change in mean arterial blood pressure over the 120 minute observation period. Additionally, when venular shear rates for the different time-points were calculated in all experimental groups, no significant differences were recorded. Thus, venular diameters ranged from 38–44 $\mu$m in all groups, and venular shear rates varied between 532±48 and 625±55 ($sec^{-1}$) in all groups. These findings clearly indicate that the adhesive interactions observed between leukocytes and endothelial cells were not due to changes in rheological factors brought about by the superfusion of the rat mesentery with L-NAME, but most likely were due to enhanced expression of cell adhesion molecules.

Figure 2:
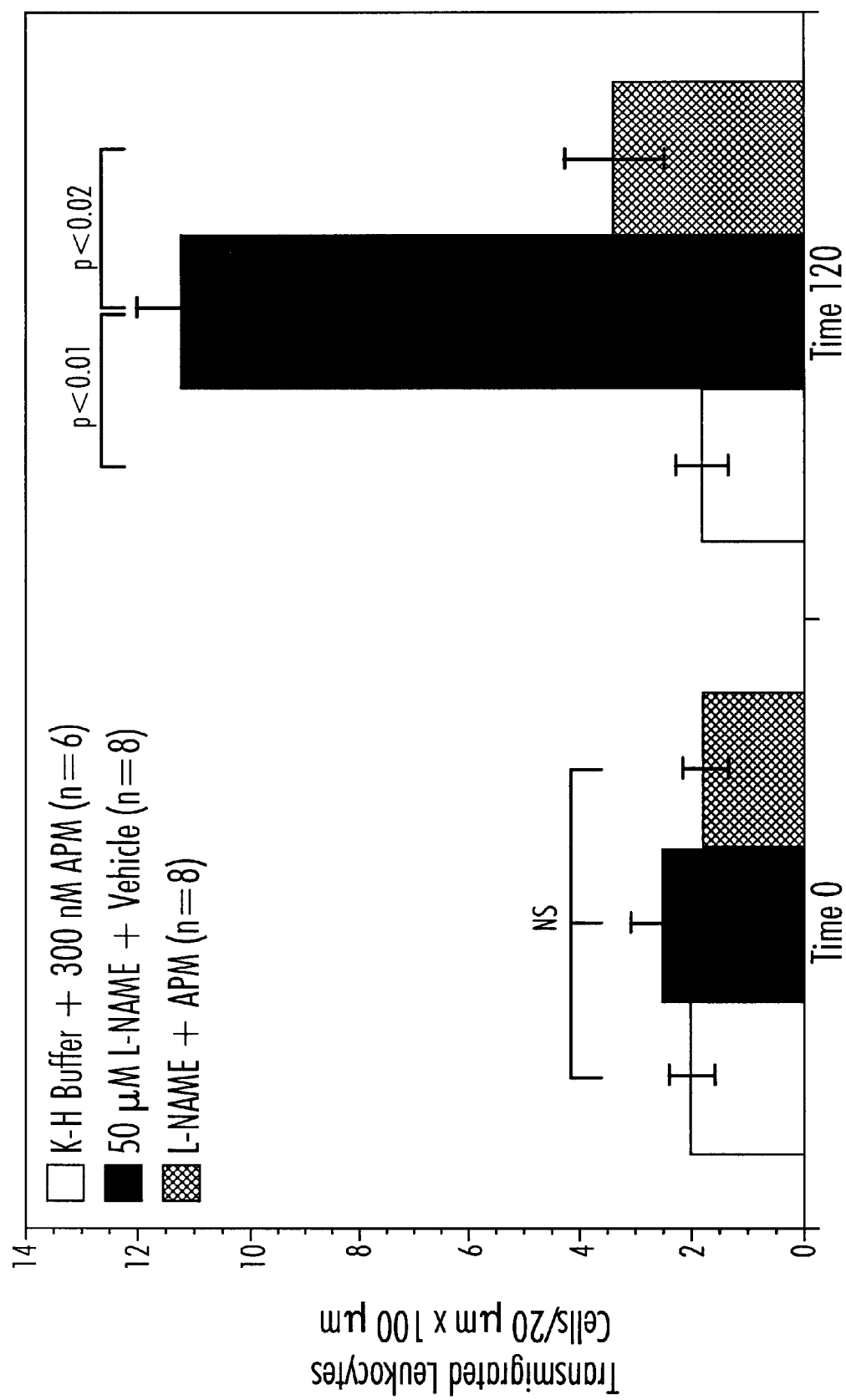
FIG. 2 shows leukocyte extravasation within a 20 mm distance from the vessel wall in the rat mesenteric microvasculature following superfusion of the mesentery with 50 μM L-NAME. Concomitant superfusion of the rat mesentery with APM attenuated L-NAME-induced extravasation of leukocyte. Bar heights show number of transmigrated leukocytes for all experimental groups of rats. All values are means ±SEM observed at 120 minutes for each group. Numbers in parentheses indicate numbers of rats studied.

A consistent low number of rolling, adhering and tansmigrated leukocytes was observed in rat mesenteries superfused with K-H buffer over the 120 minute observation period (FIG. 1, panel A). In contrast, superfusion of the rat mesentery with 50 $\mu$M L-NAME over 120 minutes resulted in a time-dependent increase in leukocyte rolling on mesenteric postcapillary neural endothelium (FIG. 1, panel A). A similar time course also was observed for leukocyte adherence (FIG. 1, panel B) and leukocyte transmigration (FIG. 2). Thus, blockade of NO synthase in the rat mesenteric circulation results in a marked increase in leukocyte-endothelium interaction, as well as leukocyte extravasation.

Concomitant superfusion f the rat mesentery with 300 nM APM markedly attenuated the L-NAME-induced increases in leukocyte rolling by 85% (FIG. 1, panel A), leukocyte adherence by 87% (FIG. 1, panel B) and leukocyte transmigration by 78% (FIG. 2).

To exclude potential nonspecific actions of the APM formulation on the observed leukocyte-endothelium interactions, the effect of AMP vehicle on leukocyte rolling, adherence and transmigration was also tested. Vehicle superfusion failed to attenuate L-NAME-induced leukocyte rolling (FIG. 1, panel A), adherence (FIG. 1, panel B) and transmigration (FIG. 2), thus confirming that the pharmacological properties observed for the active phospholipid formulation of APM were not due to nonspecific interaction of the phospholipid formulation itself with biological systems.

Figure 3:
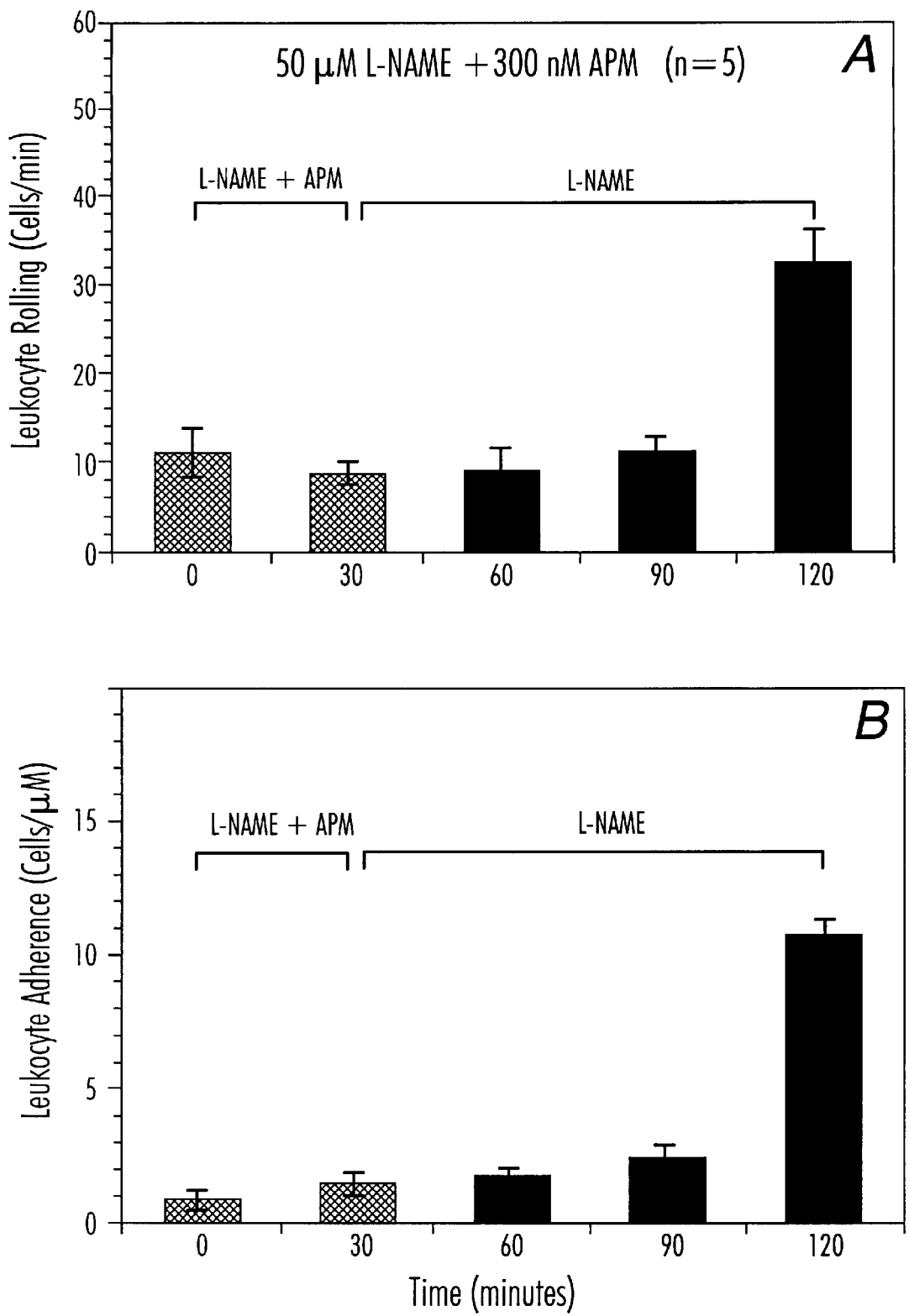
FIG. 3 shows the effect of discontinuation of APM superfusion on L-NAME induced leukocyte rolling (panel A) and leukocyte adherence (panel B). APM effects are observed up to 60 minutes after discontinuation of superfusion. Bar heights show number of transmigrated leukocytes for all experimental groups of rats. All values are means ±SEM observed at 120 minutes for each group. Numbers in parentheses indicate numbers of rats studied.

In addition, the effect of APM on leukocyte rolling and adherence (FIG. 3, panels A and B) were tested. After 30 minutes, leukocyte rolling was only 8.6±2.2 cells/min (FIG. 3, panel A) and leukocyte adherence was only 0.8±0.3 cells/100 μm venule (FIG. 3, panel B). The APM superfusion was stopped and fresh L-NAME was added. After discontinuation of APM superfusion, no increase in leukocyte rolling and leukocyte adherence was observed at both 60- and 90-minute observation times (FIG. 3). Only 30 minutes later, leukocyte rolling increased to 33±3 cells/min (FIG. 3, panel A) and leukocyte adherence increased to 11±0.7 cells/100 μm (FIG. 3, panel B). Thus, exposure of the rat mesentery to APM for a 30 minute period resulted in significant protection against L-NAME-induced leukocyte-endothelium interaction, which lasted for a period of 60 minutes.

Figure 4:
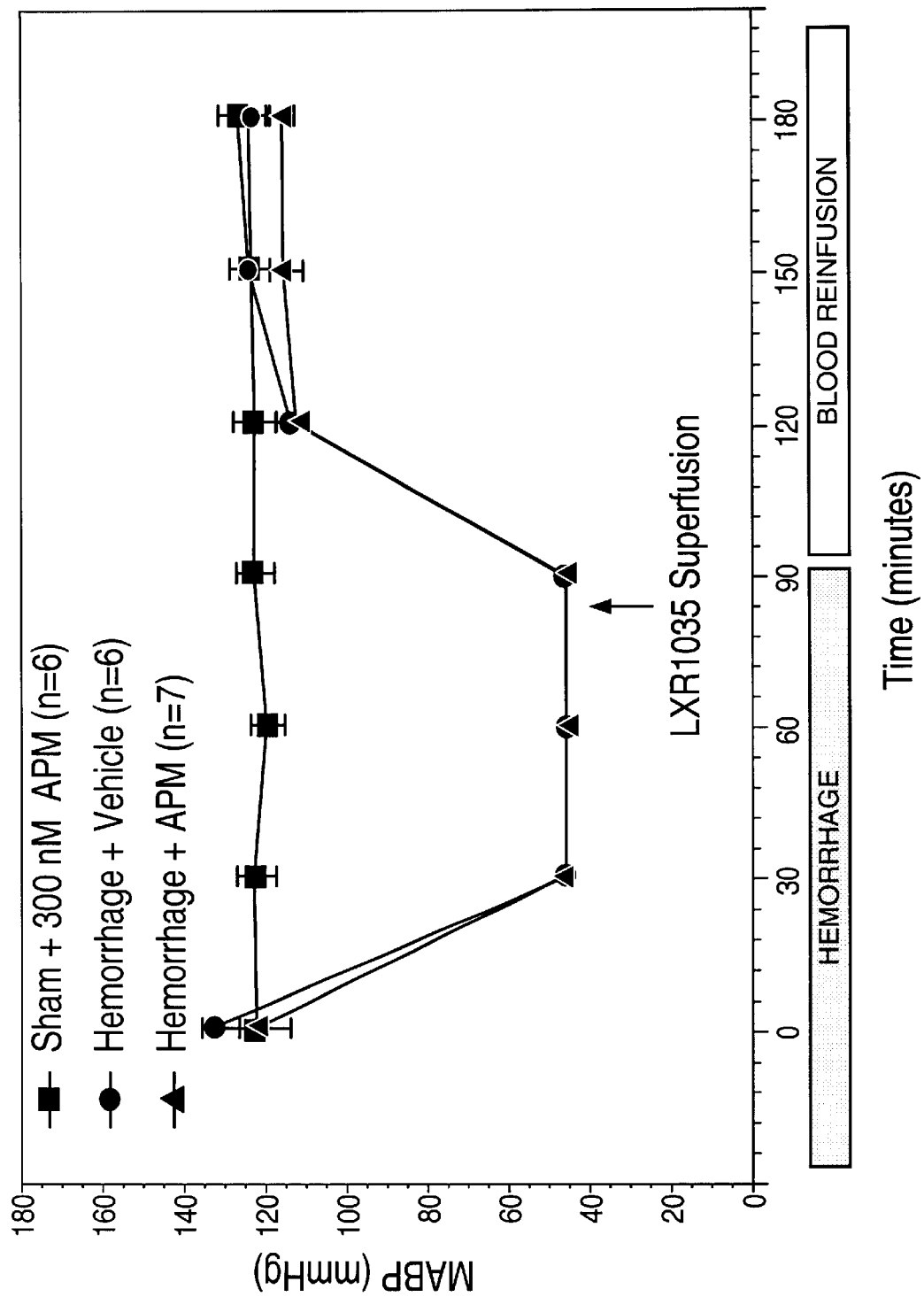
FIG. 4 shows the time course of mean arterial blood pressure over the course of hemorrhage and reinfusion for the three experimental groups of rats. Each point represents mean values ±SEM for 6–7 rats/group.

B. Effect of APM on Leukocyte-endothelium Interaction Induced by Hemorrhage-reinfusion FIG. 4 illustrates the time course of systemic MABP in the three experimental groups of rats. All groups of rats exhibited initial MABP values in the range of 120–130 mmHg. In sham operated control rats, MABP did not significantly change over the entire 180 minute observation period (FIG. 4). In hemorrhaged rats, MABP was maintained at 45 mmHg for 90 minutes. After reinfusion of the shed blood to hemorrhaged rats, MABP increased to values not significantly different from sham operated control rats at that time (FIG. 4).

Venular shear rates for the three experimental groups of rats are reported in Table 1. No significant differences were observed in initial shear rates among the three experimental groups of rats. Following hemorrhage, shear rates in mesenteric venules abruptly decreased to less than 90% of the observed initial control values. Therefore, the present hemorrhage shock model is characterized by a marked hypoperfusion of the splanchnic microvasculature during the oligemic phase. However, upon reinfusion of shed blood, venular shear rates returned to nearly normal values (Table 1). This result strongly suggests that blood flow was reestablished to control levels during the post-oligemic phase. Since shear rates were normal post-reinfusion, the adhesive interactions observed between leukocytes and the microvascular endothelium during resuscitation from hemorrhage could not be attributed to alterations in physical hypodynamic forces brought about by perturbations in local hemodynamics.

TABLE 1

Venular Diameter and Venular Shear Rates in Rat Mesenteric Venules

| | | | Venular Shear Rate (sec$^{-1}$) | | |
| --- | --- | --- | --- | --- | --- |
| Group | n | Venular Diameter (μm) | Baseline (0 min) | Hemorrhage (90 min) | Reperfusion (180 min) |
| Sham + 300 nM APM | 6 | 36.4 ± 3.1 | 530 ± 53 | 516 ± 43 | 521 ± 44 |
| Hemorrhage + Vehicle | 6 | 34.7 ± 1.4 | 519 ± 33 | 41 ± 24 | 404 ± 75 |
| Hemorrhage + APM | 7 | 34.4 ± 1.2 | 525 ± 44 | 63 ± 14 | 398 ± 81 |

All values are means ± SEM.
n = numbers of rats/group

Figure 5:
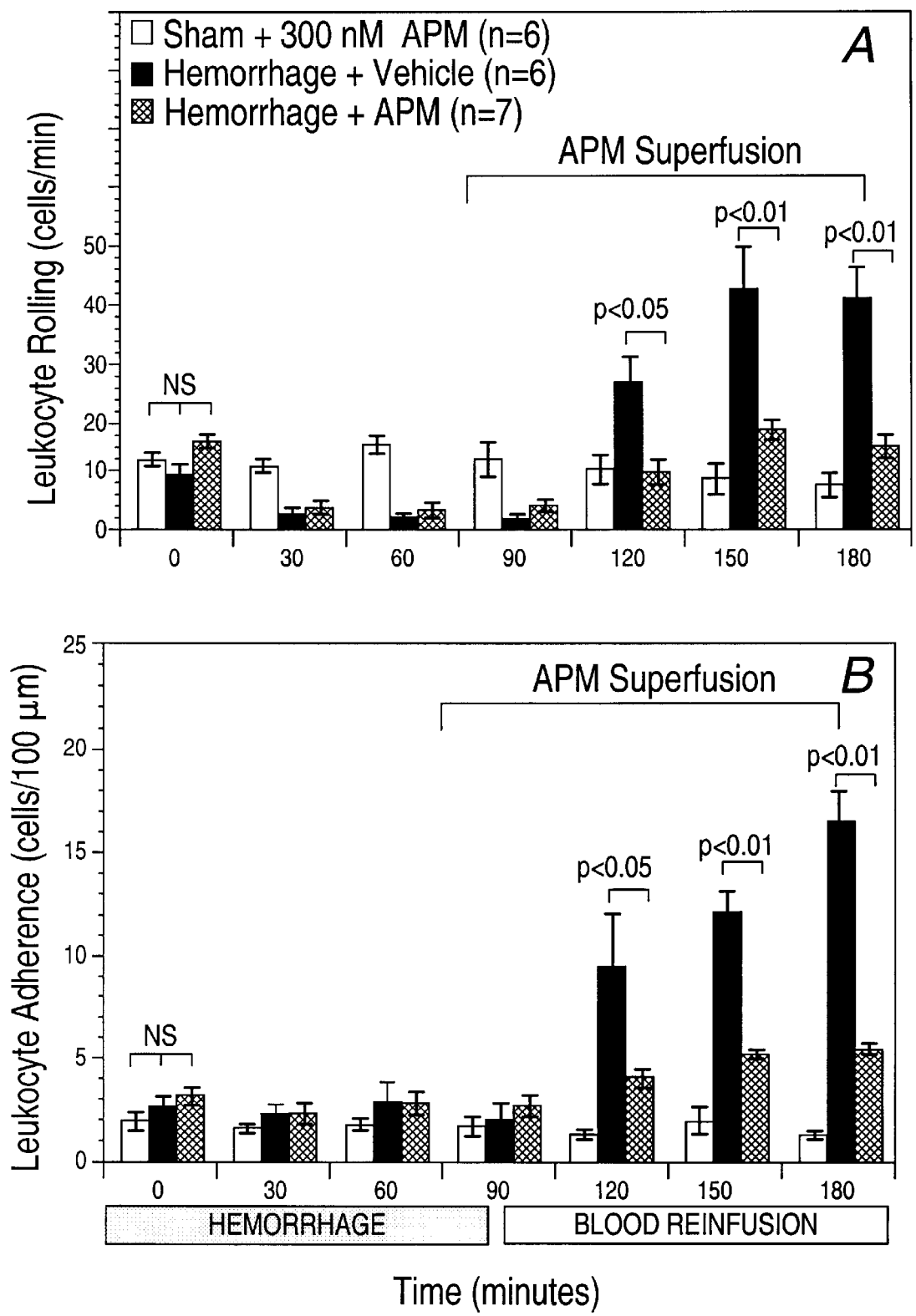
FIG. 5 shows leukocyte rolling (panel A) and leukocyte adherence (panel B) observed in mesenteric venules of sham operated rats and rats subjected to hemorrhage and reinfusion. Superfusion of the rat mesentery with APM attenuated leukocyte rolling and adherence following hemorrhage and reinfusion. Bar heights represent mean values; brackets indicate ±SEM. Numbers in parentheses indicate numbers of rats studied.
Figure 6:
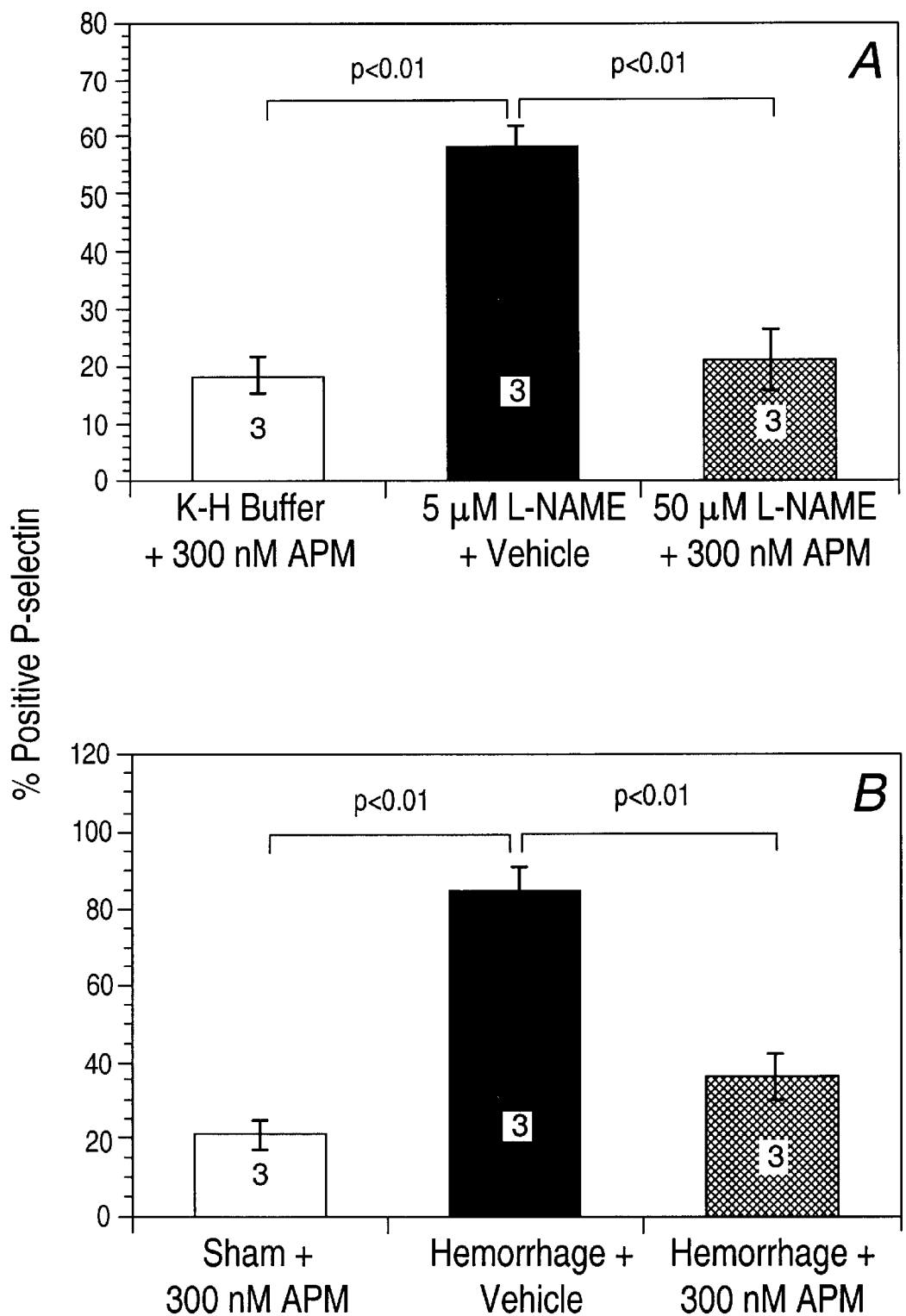
FIG. 6 shows immunohistochemical summary of P-selectin expressed on rat ileal venules. Percentage of venules staining positive for P-selectin in rat superfused with L-NAME (panel A) and rat subjected to hemorrhage and reinfusion (panel B). Superfusion of the rat mesentery with APM attenuated P-selectin expression in all experimental groups of rats. Bar heights represent mean values; brackets indicate +SEM. Numbers at the base of bars indicate the numbers of rats studied in each group. Twenty sections were studied in each rat.
Figure 7:
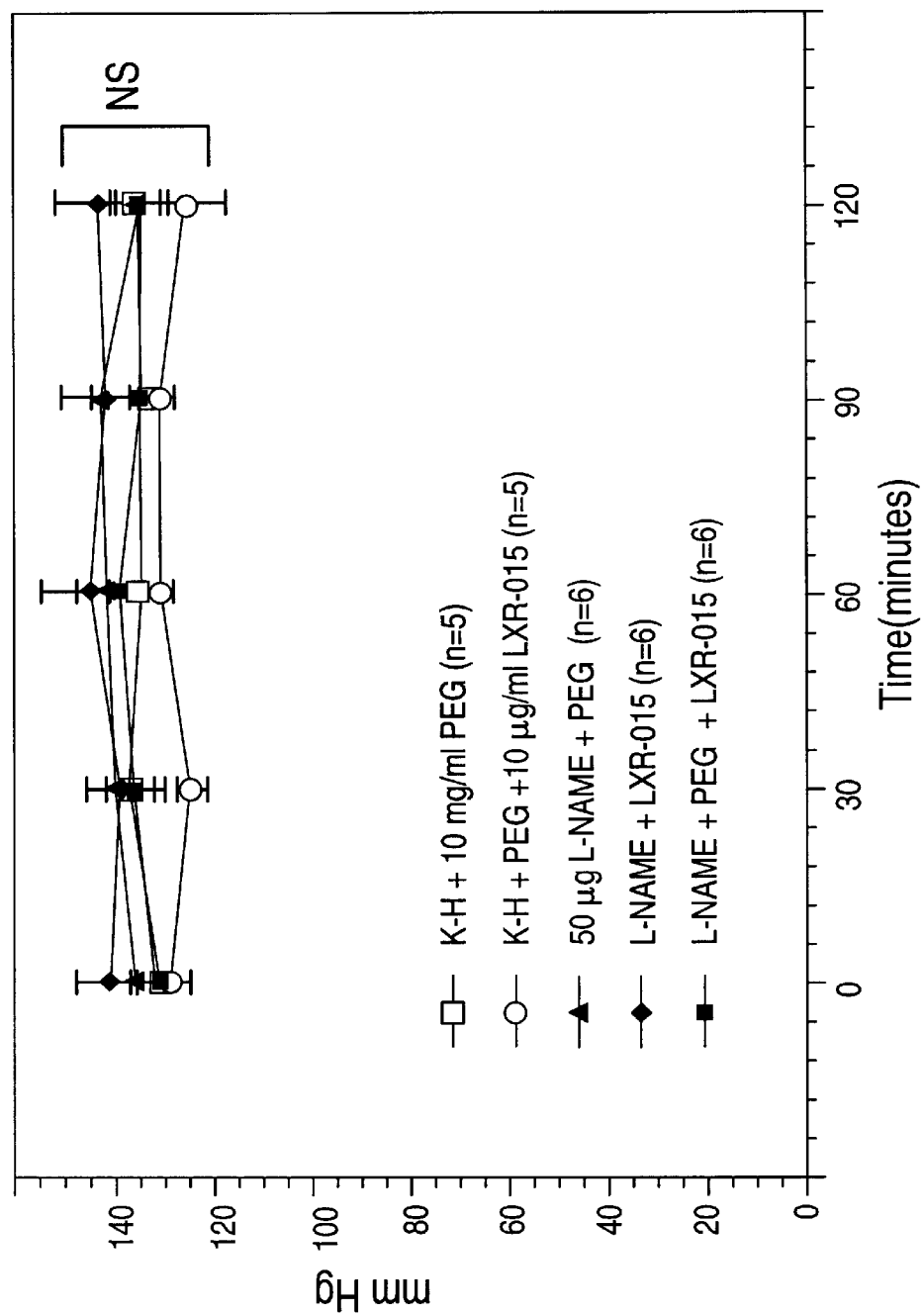
FIG. 7 shows the time course of the effect of test and control formulations on the mean arterial blood pressure in rats. Numbers in parentheses indicate the numbers of rats studied in each group.
Figure 8:
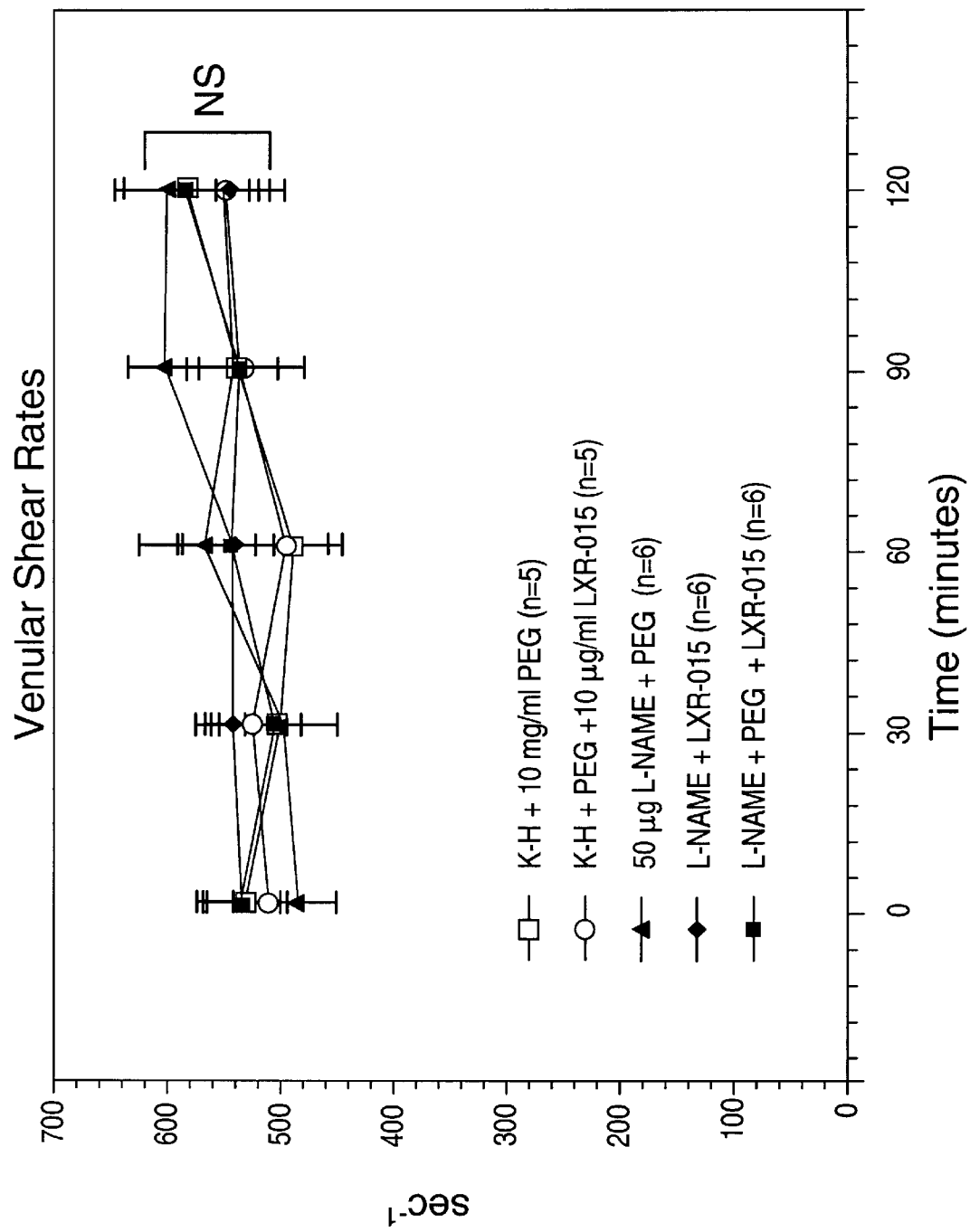
FIG. 8 shows the time course of the effect of test and control formulations on the venular shear rates in rats. Numbers in parentheses indicate the numbers of rats studied in each group.
Figure 9:
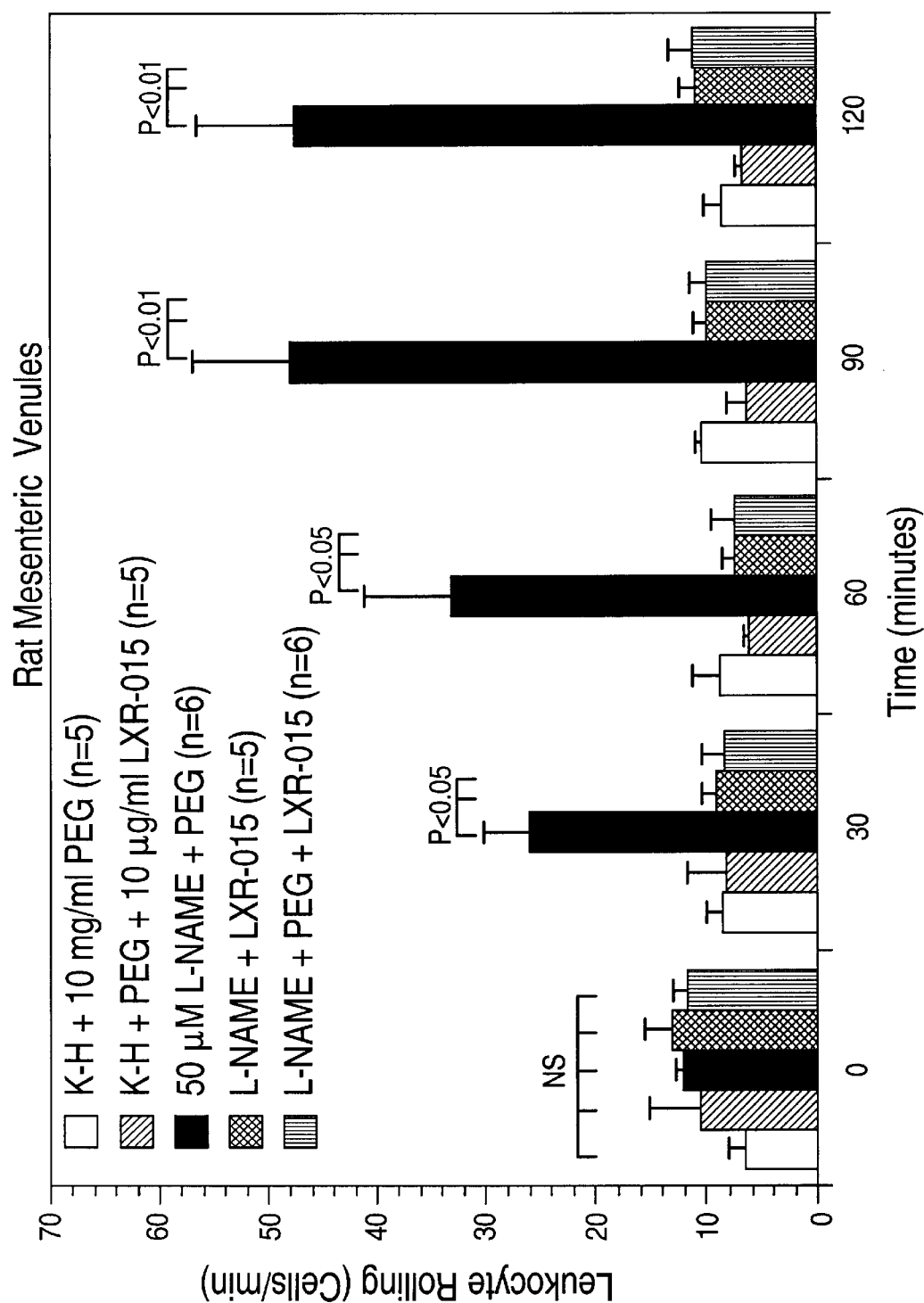
FIG. 9 shows the effect of test and control formulations on leukocyte rolling in rat mesenteric venules. Numbers in parentheses indicate the numbers of rats studied in each group. Bar heights represent mean values; brackets indicate ±SEM.
Figure 10:
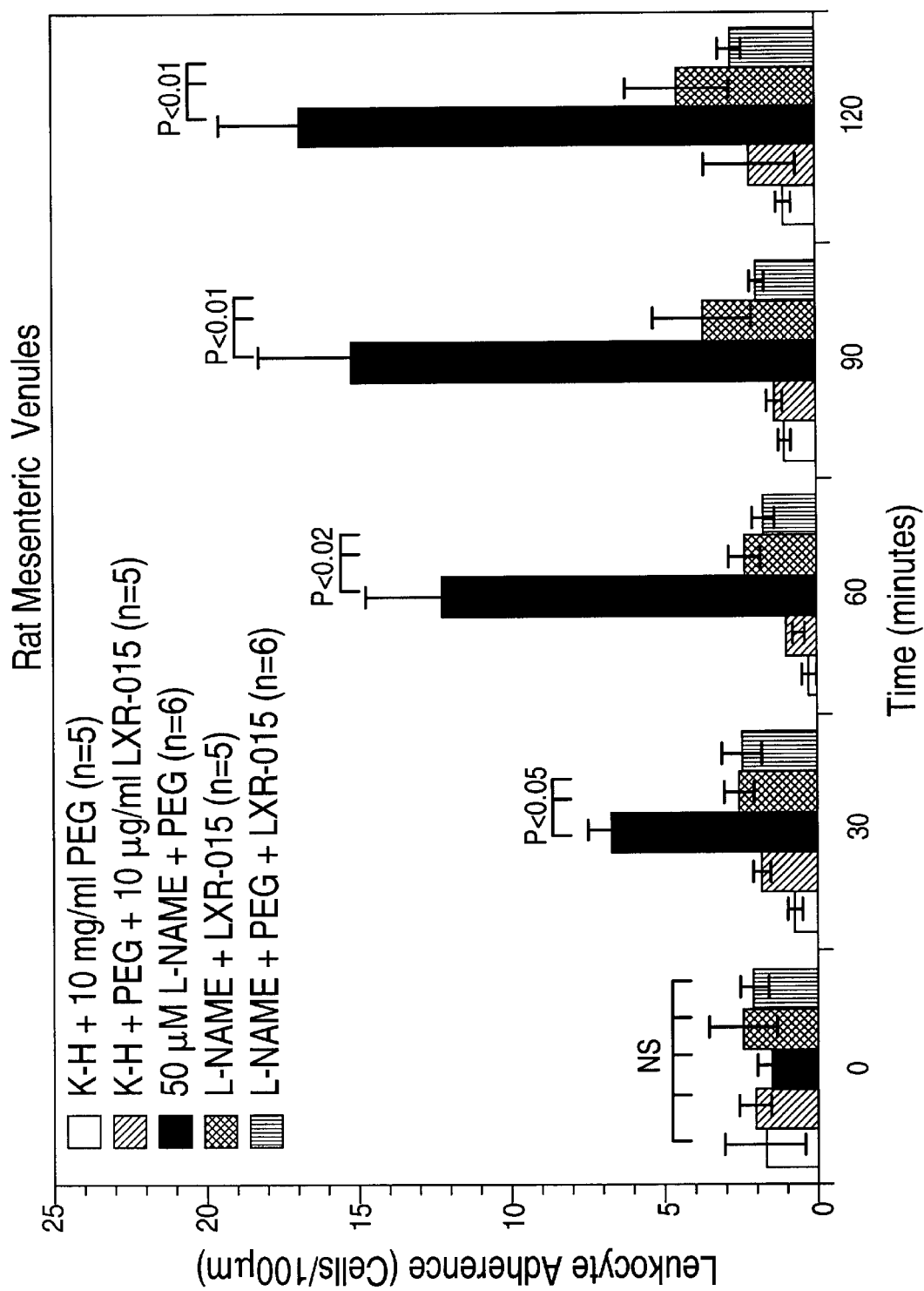
FIG. 10 shows the effect of test and control formulations on leukocyte adherence in rat mesenteric venules. Numbers in parentheses indicate the numbers of rats studied in each group. Bar heights represent mean values; brackets indicate ±SEM.
Figure 11:
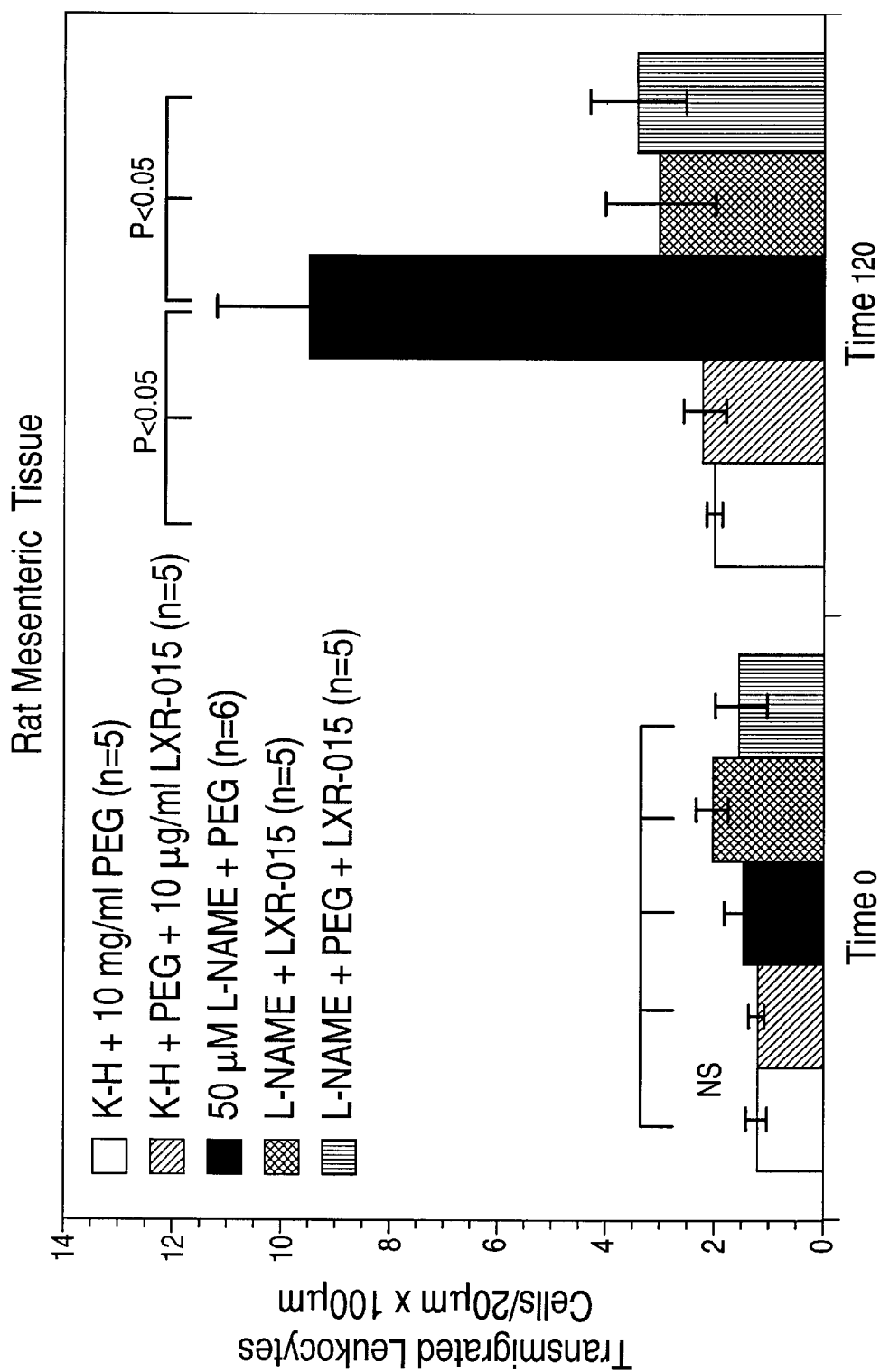
FIG. 11 shows the effect of test and control formulations on leukocyte transmigration into rat mesenteric tissues after 120 minutes. Numbers in parentheses indicate the numbers of rats studied in each group. Bar heights represent mean values; brackets indicate ±SEM.

A low baseline number of rolling (i.e., 10–20 cells/min.) (FIG. 5, panel A) and adherent (i.e., 2–3 cells/100 μm) (FIG. 5, panel B) leukocytes was observed in the mesenteric microvasculature for all experimental groups of rats. However, the number of rolling and adherent leukocytes in untreated hemorrhaged rats exhibited a four-fold (p<0.0 1) increase following reinfusion compared to normal control values (FIG. 5, panels A and B). In contrast, no significant increase in the number of rolling or adhered leukocytes was observed in the mesenteric venules of APM superfused rat mesenteries (FIG. 6, panels A and B). A similar pattern was observed also in the case of leukocyte transmigration. In addition, no significant change in the total number of circulating leukocytes was observed I the three experimental groups of rats, so that the changes in rolling and adherence could not be attributed to leukopenia. The average number of circulating leukocytes in sham operated control rats and hemorrhage rats were 8.9±0.6 and 8.5±1.4 10$^3$ cells/mm$^3$ (mean±SEM), respectively. These values are not significantly different from each other, nor was leukopenia observed at the end of the experimental protocol or following superfusion of the mesenteric tissue with 300 nM APM. Therefore, APM significantly attenuated leukocyte-endothelium interaction in the rat mesenteric microcirculation following hemorrhage and reinfusion.

C. Immunolocalization of P-selectin in the Rat Mesenteric Microvasculature

Localization of P-selectin was accomplished using a modified avidin-biotin immunoperoxidase technique. Positive staining was observed only on the venular endothelium in the rat ileum. The percentages of venules staining positive for P-selectin in ileal sections from sham-operated control rats was consistently low in the range of 20% (FIG. 6, panels A and B). Superfusion of the mesentery and ileum with 50 μM L-NAME for 120 minutes (FIG. 6, panel A), as well as hemorrhage followed by reinfusion (FIG. 6, panel B), resulted in a significant increase in P-selectin expression as quantified by the percentage of venules staining positive for P-selectin. This increase in expression of P-selectin on ileal venules was significantly attenuated by the superfusion of the mesenteric and ileal tissue with 300 nM APM (FIG. 6, panels A and B). Thus, APM markedly attenuated P-selectin expression on the venular endothelial cell surface of the rat mesenteric microvasculature.

D. Flow Cytometric Analysis of P-selectin Expression

The in vitro effects of APM were examined on rat isolated neutrophil CD18 expression after stimulation with 100 nM LTB4. Non-stimulated rat neutrophils exhibited little neutrophil surface binding of the anti-CD18 monoclonal antibody (19±1.6% positive staining). However, after incubation with 100 nM $LTB_4$, the binding of mAB anti-CD18 to neutrophils was significantly increased to 80±7.3% positive staining ($p<0.001$ vs unstimulated control neutrophils). Ten minutes after preincubation of rat neutrophils with 300 nM APM, CD18 expression was significantly attenuated in response to $LTB_4$-stimulated neutrophils). Thus, APM specifically inhibited CD18 expression on cell surfaces.

E. Discussion

The study as described herein demonstrates that nanomolar concentrations of APM significantly inhibit leukocyte-endothelial cell interaction in the rat mesenteric microvasculature during acute inflammatory events. These conclusions are based on the following observations: (a) APM inhibits L-NAME induced leukocyte-endothelium interaction in vivo; (b) exposure of mesenteric venules to APM inhibits leukocytes-endothelium interactions elicited by ischemia-reperfusion; and (c) APM down-regulates cell surface expression of two important adhesion molecules that are critical in the regulation of cell-to-cell interaction (i.e., P-selectin on the microvascular endothelium and CD18 on circulating neutrophils).

Since Umansky et al. (Umansky et al., 1997) first demonstrated that a phosphatidic acid-containing formulation (i.e., LXR-015) is capable of specifically preventing apoptotic cell death in rat neonatal cardiomyocytes exposed to simulated ischemia-reperfusion, others have shown that LXR-015 is able to attenuate tissue injury following ischemia-reperfusion of the heart in vivo (Umansky & Tomei, 1997), and to improve hypothermic preservation of ischemic rat liver during experimental transplant procedures (Wu et al., 1997). However, the precise mechanism of the protective effect of these phosphatidic acid-containing formulations in vivo remained to be determined.

The present invention relates to the discovery of the protective mechanism of APM during acute inflammatory events of the microcirculation. In particular, strong evidence is provided that APM is able to attenuate enhanced leukocyte-endothelium interaction induced by inflammatory stimuli via down-regulation of adhesion molecules expressed on the vascular endothelium, as well as on circulating neutrophils.

Recent studies on the leukocyte and endothelial adhesion molecules involved in the acute inflammatory response indicate a complex pattern of leukocyte-endothelium interaction that precedes emigration of leukocytes from the vasculature into the surrounding tissue. Leukocyte-endothelium interaction now is known to be a multistep process involving sequential activation of specific cell adhesion molecules (Bevilaqua & Nelson, 1993; McEver, 1992).

In the present study, endothelial cells were activated in vivo by either superfusing the rat mesentery with the NO synthesis inhibitor, L-NAME, or by inducing whole body ischemia-reperfusion. Acute endothelial dysfunction associated with enhanced leukocyte-endothelium interaction is a critical early pathophysiological event resulting from both inhibition of NO synthesis (Scalia & Lefer, 1998) and hemorrhage-reinfusion (Scalia et al., 1999). In addition, L-NAME has been effectively used to up-regulate leukocyte-endothelium interaction because the increased adherence mediated by L-NAME is not due to direct leukocyte activation (Kubes et al., 1991). Despite the fact that L-NAME inhibits NO synthase primarily in endothelial cells, up-regulation of P-selectin leads to enhanced leukocyte-endothelium interaction, which, in turn, leads to subsequent leukocyte activation (Davenpeck et al., 1994).

In the results reported herein, APM significantly reduced both L-NAME- and hemorrhage reinfused-provoked P-selectin expression in mesenteric endothelial cells, and therefore, attenuated leukocyte rolling, adherence and transmigration in the mesenteric microcirculation. In addition, incubation of isolated rat neutrophils with APM attenuated $LTB_4$-induced upregulation of the CD18 on the cell surface of circulating neutrophils. These results agree with earlier in vitro observations, which demonstrated that phospholipid-containing formulations exert a potent protective effect in ischemic-reperfused tissue (Umansky et al., 1997; Wu et al., 1997), thus explaining many of the pharmacological activities attributed to APM in experimental models of inflammation.

Taken together, the data generated by the present study clearly support the discovery that APM is a potent inhibitor of surface expression cell adhesion molecules. This may be a key mechanism by which APM inhibits leukocyte-endothelial interaction in inflammation.

EXAMPLE 7

Effect of APM on Adhesion to the Mesenteric Endothelium

Figure 13:
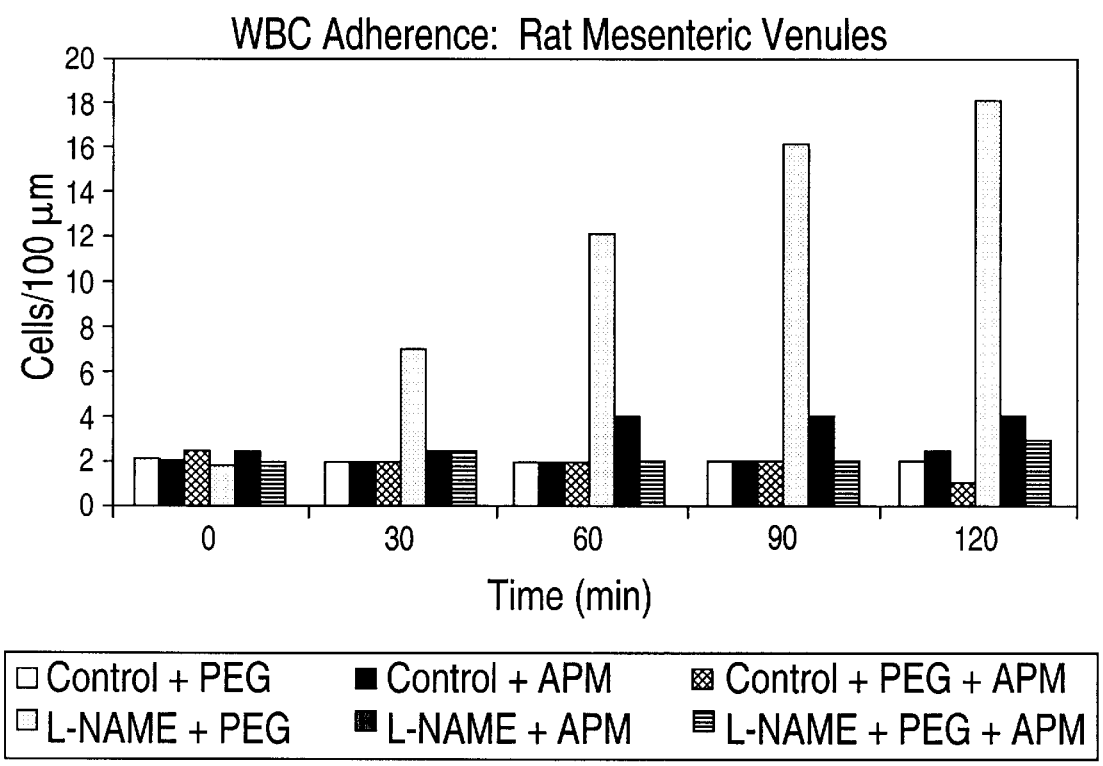
FIG. 13 shows the effect of APM on leukocyte adherence in rat mesenteric venules. The SEM appeared to be within 5–10% of the means. L-NAME+APM and L-NAME+APM+PEG groups are the mean of 6 independent experiments, while the other groups are the mean of 5 independent experiments.

Additional studies were conducted in which data shows that APM in the superfusate at 10 μg/mL (approximately 5 μM LPA) almost completely blocked the occurrence of both rolling and adherence. Adherence is shown in FIG. 13 at 0, 30, 60 90 and 120 minutes post treatment with L-NAME. Although not shown in FIG. 13, L-NAME alone did not significantly differ from L-NAME+PEG (10 mg/mL). Thus, PEG appears to have little or no effect on this measure of inflammation. APM+PEG did give a consistent, but statistically insignificant decrease in adherence compared with APM only.

Additional studies demonstrated in vitro that LXR-1035 (rac-1-thiophosphate-2-O-methyl-3-oleioyl-glycerol) at 300 nM also resulted in a similar inhibitory effect on leukocyte adherence as APM. In vitro, LXR-1035 also inhibits the cell surface expression of the adhesion molecule CD18, which plays a role in the firm binding of leukocytes to endothelial cells manifested as adherence.

EXAMPLE 8

Effect of LXR-015 on Leukocyte-endothelial Cell Interactions

The effect of LXR-015 on leukocyte-endothelial cell interactions was studied using intravital microscopy of the rat mesentery as described above. Superfusion of the rat mesentery with 50 μM L-NAME caused a significant, time-dependent increase in leukocyte rolling, adherence, and transmigration compared to control rats superfused with Krebs-Henseleit (K-H) solution (FIGS. 7–11). However, superfusion of the rat mesentery with 10 μg/ml LXR-015 consistently inhibited the L-NAME-induced leukocyte rolling, adherence, and transmigration, without altering systemic blood pressure or mesenteric venular shear rates (FIGS. 7–11).

To exclude potential nonspecific actions of the LXR-015 formulation on the observed leukocyte-endothelium interactions, the effect of a 10 μg/ml PEG, the specific vehicle for LXR-015, on leukocyte rolling, adherence and transmigration was also tested. Vehicle superfusion failed to attenuate L-NAME-induced leukocyte rolling, adherence, and transmigration (FIGS. 7–11), thus confirming the pharmacological properties observed for the active phospholipid formulation of LXR-015 were not due to nonspecific interaction of the phospholipid formulation itself with biological systems.

Figure 12:
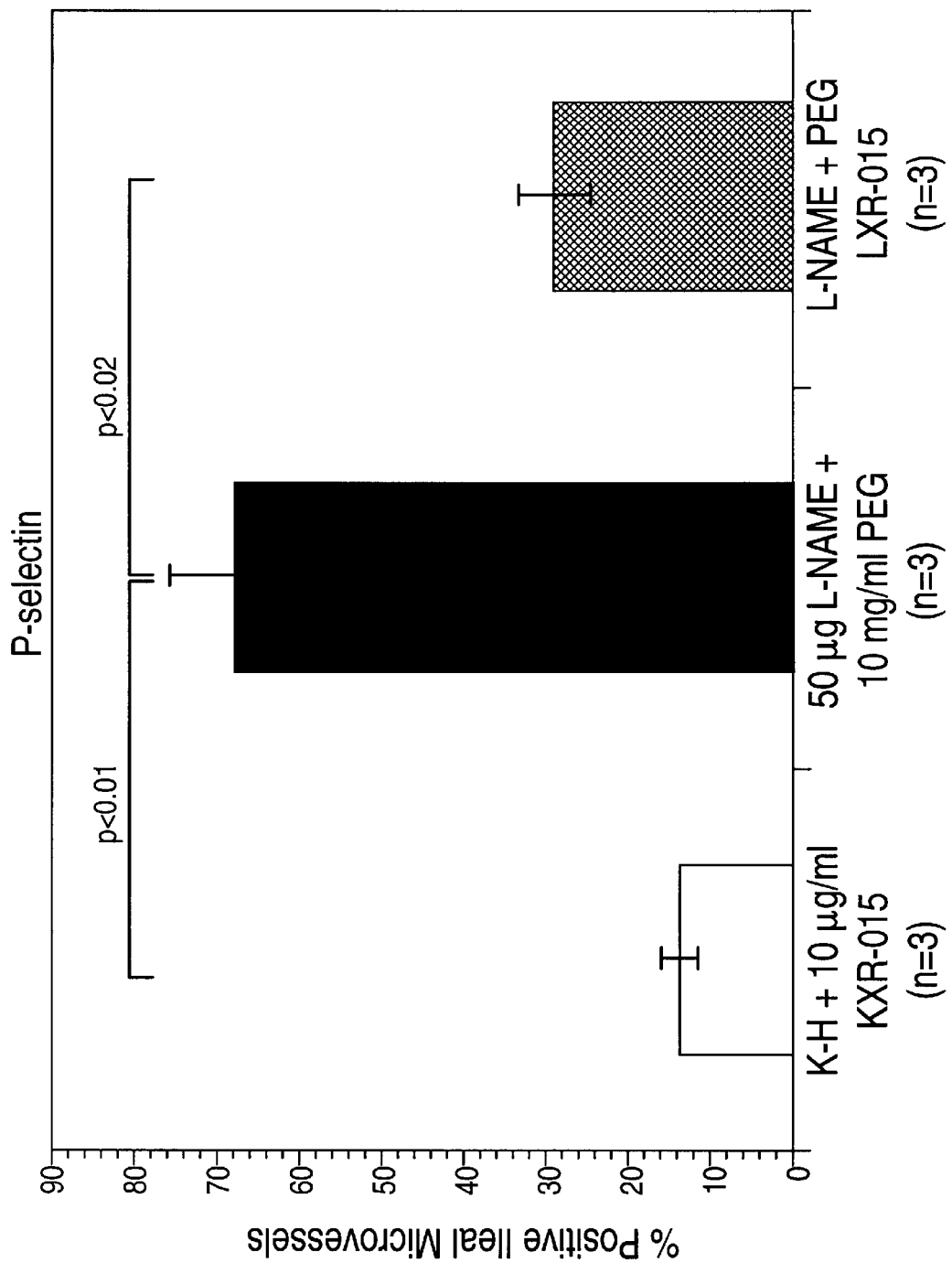
FIG. 12 shows the immunohistochemical localization of P-selectin expression on mesenteric venules after exposure to L-NAME. Bar heights represent mean values; brackets indicate ±SEM.

Immunohistochemical localization of P-selectin expression on mesenteric venules was significantly increased after exposure to L-NAME, which was significantly attenuated by LXR-015 (p<0.02) (FIG. 12). These data clearly demonstrate that LXR-015 can potently reduce pathological recruitment of leukocytes in the mesenteric rat microvasculature by attenuating endothelial cell surface expression of P-selectin.

While various embodiments of the present invention have been described in detail, it is apparent that modifications and adaptations of those embodiments will occur to those skilled in the art. For example, the osteoinductive factors can be used in various applications such as treating periodontal diseases and in facial reconstruction, as well as in treating other bone and joint problems. However, it is to be expressly understood that such modifications and adaptations are within the spirit and scope of the present invention, as set forth in the following claims.

What is claimed is:

1. A method to regulate expression of adhesion molecules on circulating leukocytes of a mammal, comprising administering to said mammal a composition comprising a mixture of soy-derived phospholipids.

2. A method, as claimed in claim 1, wherein said mixture of soy-derived phospholipids comprises a mixture of phosphatidic acid (PA), phosphatidyl inositol (PI), lysophosphatidic acid (LPA), lysophophatidyl choline (LPC) and lysophosphatidyl inositol (LPI).

3. A method, as claimed in claim 2, wherein said mixture of soy-derived phospholipids comprises a mixture of phosphatidic acid (PA), phosphatidyl inositol (PI), lysophosphtidic acid (LPA), lysophosphatidyl choline (LPC) and lysophosphatidyl inositol (LPI) in a ratio by weight of 10:10:8:4:2.

4. A method, as claimed in claim 1, wherein said mixture of soy-derived phospholipids comprises LXR-015.

5. A method, as claimed in claim 1, wherein said adhesion molecules are cell adhesion glycoproteins.

6. A method, as claimed in claim 1, wherein said adhesion molecules are selected from the group consisting of integrins, immunoglobulin superfamily members and selectins.

7. A method, as claimed in claim 1, wherein said mammal is a human.

8. The method of claim 1, wherein the expression of said adhesion molecules is down-regulated.

* * * * *